United States Patent [19]

Jula et al.

[11] 4,010,757

[45] Mar. 8, 1977

[54] AUXILIARY TOOL FOR REMOVING ELECTRODE FROM HOLDER

[76] Inventors: James L. Jula, 3880 Oak Terrace, White Bear Lake, Minn. 55110; Dennis E. Zeidler, 1835 134th Lane NE., Anoka, Minn. 55303

[22] Filed: Jan. 24, 1975

[21] Appl. No.: 543,810

Related U.S. Application Data

[62] Division of Ser. No. 443,802, Feb. 19, 1974, Pat. No. 3,875,947.

[52] U.S. Cl. .......................... 128/418; 128/419 P; 81/3 R; 254/104
[51] Int. Cl.² .......................................... A61N 1/02
[58] Field of Search ............... 128/418, 419 P, 404, 128/214, 329 R, 347; 279/1 E; 254/104; 81/3 R, 3.48, 3.49; 29/253; 66/116, 117

[56] References Cited

UNITED STATES PATENTS

| 300,423 | 6/1884 | Wild | 254/104 |
|---|---|---|---|
| 3,362,408 | 1/1968 | Stocki et al. | 128/314 |
| 3,615,955 | 10/1971 | Mirowski | 128/419 P |
| 3,737,579 | 6/1973 | Bolduc | 128/419 P |
| 3,754,555 | 8/1973 | Schmitt | 128/419 P |

FOREIGN PATENTS OR APPLICATIONS

| 1,039,854 | 1/1951 | France | 81/3.49 |
|---|---|---|---|
| 278,957 | 8/1970 | U.S.S.R. | 128/418 |

*Primary Examiner*—Robert W. Michell
*Assistant Examiner*—Lee S. Cohen

[57] ABSTRACT

An auxiliary tool for use with a primary tool employed in implanting an electrical lead in body tissue, the primary tool being designed to hold the lead during implantation so as to avoid imparting torque to the lead, such primary tool including a slotted end, a longitudinally extending groove and a longitudinally extending bore which communicates with the groove and the slotted end. The auxiliary tool, which includes a body portion moveable in the bore, a ridge portion moveable in the groove, and a terminal portion moveable in the slotted end, serves to remove the lead from the primary tool after implantation of the electrode.

1 Claim, 5 Drawing Figures

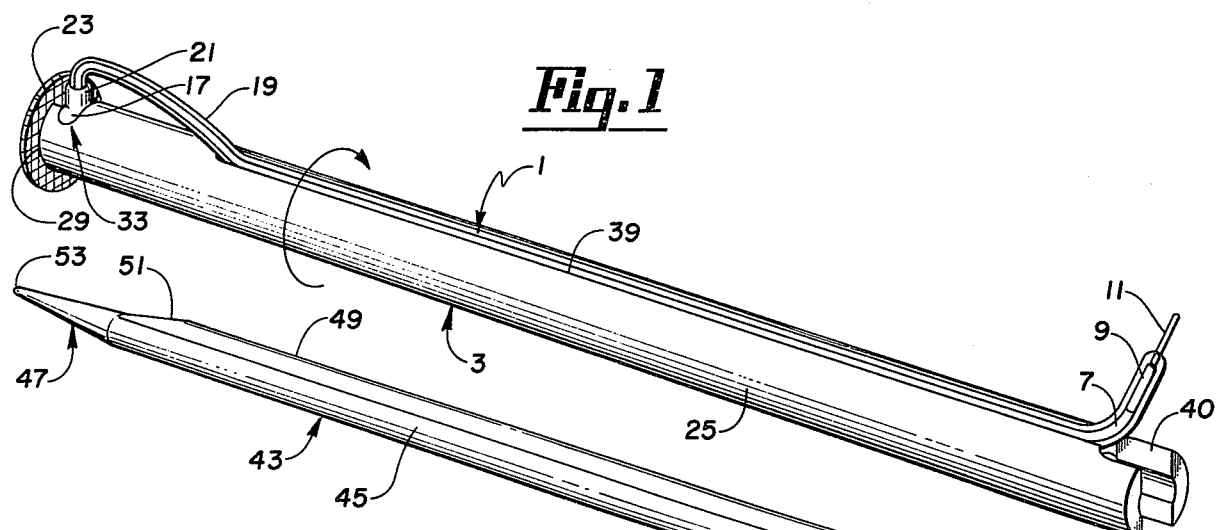
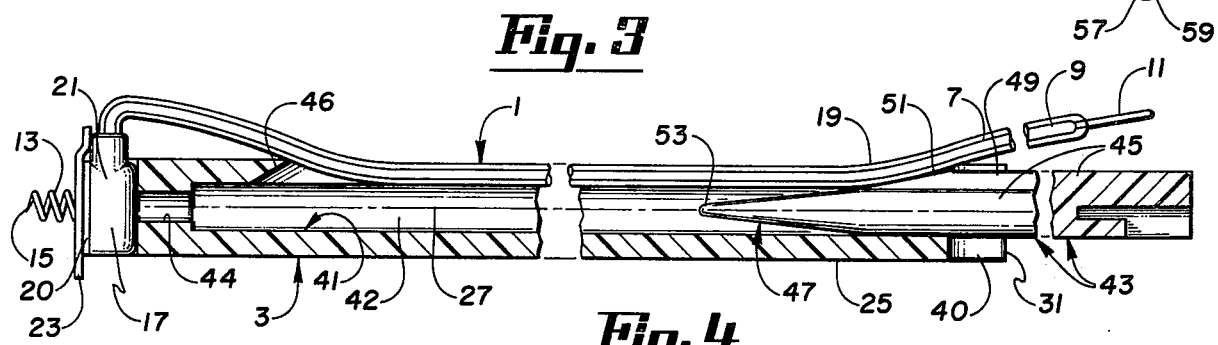
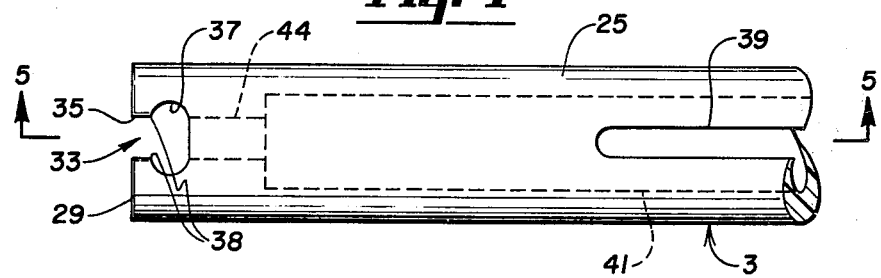
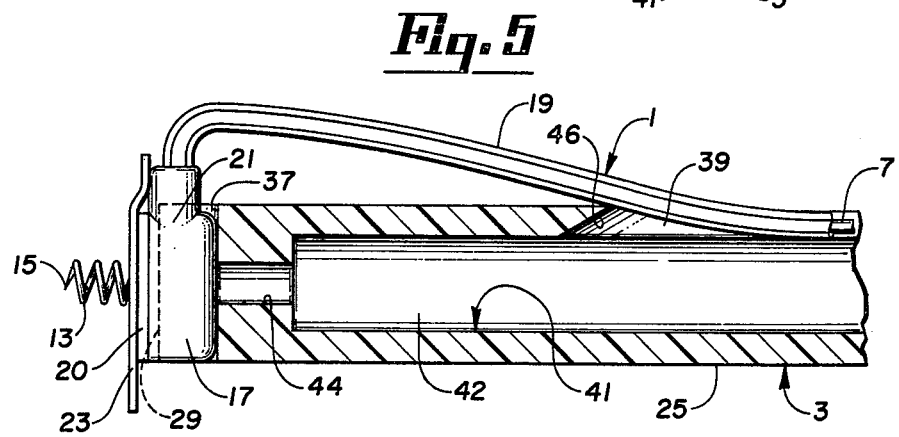

AUXILIARY TOOL FOR REMOVING ELECTRODE FROM HOLDER

This application is a division of copending U.S. Ser. No. 443,802, filed Feb. 19, 1974 now U.S. Pat. No. 3,875,947.

BACKGROUND OF THE INVENTION

This invention relates to the field of medical electronics and particularly to an improved device for handling electrical leads having implantable body tissue electrodes.

U.S. Pat. No. 3,737,579 discloses a device or tool for holding an electrical lead during body implantation in such a manner that by rotating the tool the helix-shaped electrode can be screwed into place without imparting torque to the lead along its entire length. The lead or electrode assembly includes three funtionally distinct sections: (1) an implantable, conductive helix-shaped electrode affixed to an insulated boot, (2) a flexible, insulatingly covered conductor, and (3) a plug or connector for connection to a power source. The device or tool for holding this lead disclosed in the above-mentioned patent includes three elements which serve to hold the lead during implantation—a slotted end, a longitudinally extending groove, and a bore extending the length of the tool, and parallel to the groove. The slotted end has straight, uniplanar sides dimensioned to accommodate the boot with enough compression to retain the boot in the slot during the implantation procedure yet permitting removal of the boot from the slot without disturbing the implanted helix. While the boot member has proved satisfactory, some problems have been encountered in retaining the boot in the slot if the boot and/or the slot is wet, especially prior to initially positioning the boot in the slot.

The longitudinally extending groove of the former device accommodates the flexible, insulatingly covered conductor during implantation while the bore receives the connector. Once the helix-shaped electrode is implanted in the body tissue, the lead is disengaged from the tool in three steps; first, removal of the connector from the bore; second, removal of the boot member from the slotted end; and third, removal of the flexible conductor from the groove. The second step is preferably accomplished by an auxiliary tool shaped like a knitting needle which is inserted through the bore until the end of the needle-shaped tool pushes the electrode boot out of the slot. This operation does not, however, simultaneously remove the flexible, insulatingly covered conductor from the groove. Depending upon the tightness of the grip between the outer surface of the flexible conductor and the groove, freeing of the flexible conductor can be a cumbersome task in the surgical environment.

In the present invention, there is provided a device for use in screwing the conductive uninsulated distal end portion of a body implantable electrode assembly into body tissue, said assembly being of the type including a flexible insulated electrical conductor having a proximal end thereof adaptable for connection to a power supply, said device comprising: (1) first means for firmly holding a portion of said electrode assembly near said uninsulated distal end portion thereof, (2) second means adapted to contact an insulated portion of said insulated conductor for releasably holding said conductor to facilitate the screwing of said distal end portion into body tissue and for preventing the transmission of torque to said proximal end of said conductor means when said distal end portion is being screwed into body tissue, and (3) third means communicating with said first and second means whereby said electrode is releasable from said first and second means by means locatable in said third means.

A second or auxiliary device for use in combination with the above-defined primary device is also provided, such auxiliary device including a first portion moveable in the third means of the primary device, a second portion associated with the first portion and moveable in the second means of the primary device, and a third portion moveable into the first means of the primary device whereby movement of the auxiliary device into operative position with respect to the primary device removes the implantable electrode from the primary device. As will be seen hereinafter, this auxiliary device permits the boot-shaped distal end of the lead to be removed from the slotted end of the primary device in the same operation as the flexible, insulatingly covered conductor from the groove of the primary device.

Drawings are provided wherein:

FIG. 1 is a perspective view of the primary device of this invention holding an implantable lead;

FIG. 2 is a perspective view of the auxiliary device of this invention;

FIG. 3 is a transverse sectional view of the primary and auxiliary devices in an operative position;

FIG. 4 is an enlarged top view of the working end of the primary device; and

FIG. 5 is a sectional view taken along lines 5—5 of FIG. 4.

In FIG. 1 an implantable lead 1 is held by device 3. Lead 1, which is essentially the same as lead 10 depicted in FIG. 1 of U.S. Pat. No. 3,737,579, includes a flexible conductor 7 of wrapped platinum wire or other suitable conducting material adaptable to the internal environment of a human or animal body.

Affixed to the proximal end of conductor 7 is an electrical connector 9 having a tip or extension 11 which may be connected to a suitable implantable or external power supply. Affixed to and serving as the distal end portion of conductor 7 is a rigid helical electrode 13 (see FIG. 3) having several convolutions. Helical electrode 13 is a rigid coil which may, for example, be made of platinum/irridium and terminates in a sharply pointed end 15. Electrode 13 serves as the distal end portion of conductor 7 which may be screwed into body tissue as will be explained later. Electrode 13 and conductor 7 are electrically joined together by conductive epoxy (not shown) substantially orthogonally with respect to one another and this electrical junction is contained in a rubber boot 17.

Conductor 7, connector 9 and boot 17 are covered with a relatively transparent, flexible, insulating covering being relatively inert with respect to the body, which, for example, may be a silicone rubber casing 19. The portion of casing 19 surrounding boot 17 forms a raised portion or projection 21. The distal portion of casing 19 is terminated and shaped as a circular disc 20 through which helical electrode 13 projects. Helical electrode 13 projects through the disc 20 at substantially a right angle to conductor 7. Affixed to the under surface of the disc is a circular sheet of netting 23, which may, for example, be made of Dacron, a trademark of E. I. DuPont DeNemours and Company for a type of polyester fiber. Netting 23 enhances fibrotic growth, further insuring a secure connection of the electrode to the tissue.

The device 3 is adapted to hold lead 1 at three places; the boot 17, casing 19, and connector 9. Device 3 comprises a substantially cylindrically-shaped body 25 having a longitudinal axis 27 and end surfaces 29 and 31. Device 3 may be made, for example, of a hard plastic material such as Delrin, a trademark of the E. I. DuPont DeNemours and Company for acetal resins. Preferably device 3 should be made of an autoclavable material. Formed in end surface 29 is a slot 33. Slot 33 includes a frontal opening 35 leading to a cavity 37. The width of cavity 37 is greater than the width of frontal opening 35. The widths of frontal opening 35 and cavity 37 are selected such that boot 17 must be laterally compressed to a slight degree in order to pass through frontal opening 35. Once at least a portion of boot 17 is past the shoulders 38, that portion resumes its original shape. To remove boot 17 from slot 33 requires recompressing such portion in order to gain withdrawal from frontal opening 35. The shape of slot 33 and boot 17 is designed such that the force required to achieve the requisite compressive state is greater than the forces that might be encountered in the implantation procedure but insufficient to disturb the implanted electrode 13 as the boot 17 and slotted end 29 are being separated.

Formed in the outer surface of device 3, lying in a plane substantially parallel to axis 27, and extending from end surface 31 for substantially the entire length of device 3, is a groove 39. Groove 39, which is substantially aligned with slot 33, is adapted to receive and securely engage at least a portion of the length of casing 19. End surface 31 includes a slot 40 which communicates with a central bore 41. Central bore 41 includes a first section 42 which extends slightly beyond groove 39 and a second section 44 of reduced diameter which is concentric with section 42. Section 42 of bore 41 is adapted to receive at least a portion of the proximal end of lead 1 including connector 9 and tip 11. Bore 41 communicates with groove 39 the entire length of groove 39. At the approach to end 29, groove 39 provides a terminal portion 46 which slants downward towards end 29 until it merges with bore 41. As will be seen hereinafter this terminal portion of groove 39 is shaped to accommodate the terminal portion of an auxiliary tool. The cross-sectional dimension of groove 39 is preferably less than the cross-sectional dimension of section 42 of bore 41. Groove 39 is wide enough to receive and hold casing 19, yet preferably not so wide that casing 19 is able to drop into section 42 of bore 41.

In FIG. 2 there is shown an auxiliary tool 43 for use in combination with the device 3. Tool 43 includes a substantially cylindrical body portion 45, a terminal portion 47, and a ridge portion 49. Body portion 45 is designed to slide freely in bore 41 of device 3. As body portion 45 advances in bore 41 from end 31 to end 29, ridge portion 49 simultaneously advances in groove 39. Ridge portion 49 should be of such a size and shape that it is freely slidable in groove 39 and will push or wedge the casing 19 out of groove 39 as it slides along. Ridge portion 49 is preferably relatively thin, with flat, parallel side walls. The leading edge 51 of ridge portion 49 preferably slants downwardly to meet body portion 45 at the terminal portion 47. Terminal portion 47 is tapered to a centered point 53. This allows the casing 19 to be pushed forward and upward out of groove 39 rather than just forward. Terminal portion 47 is generally conically shaped with the cone apex (end 53) being sufficiently blunt so that it will push rather than penetrate boot 17 in slot 33. The terminal portion 47 is preferably of such a size and shape that the length thereof which will extend from the end of section 44 of bore 41 is approximately equal to or slightly longer than the depth of cavity 37. Auxiliary tool 43 may be constructed of the same material as device 3.

At the opposing end of terminal portion 47, tool 43 contains an aperture 55 including a circular opening 57 and a slot 59 communicating therewith leading to the outer surface of body portion 45. Aperture 55 is provided to accommodate tip 11 of lead 1. As will be explained hereinafter, after implanting the helical electrode 13 in tissue and removing lead 1 from device 3, the dangling tip 11 can be inserted into aperture 55 and tool 43 used as a tunneling device to tunnel through subcutaneous tissue to bring lead 1 to a proper position for connection at tip 11 to a suitable power supply.

FIG. 3 depicts the primary device 3 of FIG. 1 gripping the lead 1 at the slotted end 33 and partially along groove 39. Tool 43 has been inserted in bore 41 and advanced partially therealong towards slot 33. That segment of casing 19 previously located in the section of groove 39 which has been traversed by ridge portion 49 has been displaced from groove 39 whereas the remainder of casing 19 as well as boot 17 await displacement as tool 43 advances.

In explanation of the manner of using the present invention, the first step is to secure the lead 1 to the device 3 as shown in FIG. 1. The raised portion of boot 17 is fitted into frontal opening 35 with compression and then at least a portion of boot 17 pushed into cavity 37 to provide a secure hold of boot 17.

A small loop is left in the portion of casing 19 immediately proximal to boot 17 and then casing 19 is worked into groove 39 so as to be securely held in the groove against movement. Then connector 9 and tip 11 are then doubled back for insertion into bore 41 as far as they will go. In this position the electrode 13 is positioned substantially parallel to longitudinal axis 27 of device 3 and the assembly is now ready for the electrode to be screwed into body tissue.

Pointed end 15 is placed against the tissue or organ and device 3 is rotated as indicated by the curved arrow. The diameter of the wound is confined to the diameter of the wire of which helical electrode 13 is formed. As device 3 is rotated, helical electrode 13 is firmly screwed into the tissue or organ until netting 23 firmly contacts the outer surface of the organ. Netting 23 helps to provide a more secure and permanent placement of electrode 13 in the tissues in that the netting promotes more rapid fibrosis in and around the netting, as well as around the disc 20 and raised portion 21 of casing 19.

When electrode 13 is firmly screwed into the tissue and netting 23 firmly seated against the outer surface of the tissue or organ, the connector end of lead 1 is removed from bore 41. Then, the auxiliary tool 43 is utilized as described above to progressively remove the portion of casing 19 lying in groove 39, and then the boot 17 held in slot 33, thereby freeing lead 1 from device 3. With the use of the implantation procedure described, since boot 17 and a substantial portion of casing 19 are firmly secured during the rotation of device 3, no torque is transmitted to lead 1 and consequently to conductor 7. In addition, before, during, and after the insertion procedure, device 3 in no way contacts the helical convolutions of electrode 13, permitting a very positive action in screwing electrode 13 into the tissue at substantially a 90° angle.

After implantation, tip 11 may be inserted in aperture 55 of tool 43 and tool 43 then passed, terminal portion 47 end first, through subcutaneous tissue until the site is reached where tip 11 is to be connected to a power supply under the skin. The tip 11 is then removed from aperture 55 and the electrical connection made. While tool 43 may be employed for this purpose it is also possible to employ a tool of the same design and shape as tool 43 except that ridge 49 is absent, making the body substantially cylindrical in shape with the other elements of tool 43 retained.

What is claimed is:

1. An article for removing a body implantable electrode assembly from a device for holding said assembly, said assembly being of the type having an electrically conductive uninsulated distal end portion, a flexible insulated electrical conductor, and a proximal end thereof adaptable for connection to a power supply, said device including a first means for firmly holding a portion of said electrode assembly near said uninsulated distal end portion thereof, second means adapted to contact an insulated portion of said insulated conductor for releasably holding said conductor to facilitate the screwing of said distal end portion into body tissue and for preventing the transmission of torque to said proximal end of said conductor when said distal end portion is being screwed into body tissue, and third means communicating with said first and second means for allowing said electrode and said conductor to be released from said first and second means by said article, said article comprising a first portion comprising an elongated, substantially cylindrical member dimensioned to be moveable in said third means, a second portion dimensioned to be moveable in said second means, said second portion comprising a ridge member extending substantially entirely along the length of said first portion and parallel to the longitudinal axis of said first portion, and a third portion dimensioned to be moveable in said first means comprising a cone-shaped member attached to one end of and in axis alignment with said first portion, said second portion having an upwardly inclining, leading edge commencing proximate the junction of said first and third portions, whereby movement of said article into operative position removes said assembly from said first and second means, and said cylindrical member of said first portion further having aperture means located in the end remote from said third portion, said aperture means being dimensioned to receive said proximal end of said assembly.

* * * * *